(12) United States Patent
Opitz et al.

(10) Patent No.: US 6,403,553 B1
(45) Date of Patent: Jun. 11, 2002

(54) USE OF POLYPEPTIDES FOR TREATING THROMBOCYTOPENIA

(75) Inventors: Hans-Georg Opitz, Weinheim; Joachim Schmitt, Viernheim; Wolf-Georg Forssmann, Blücherstrasse 5, D-30175, Hannover; Peter Schultz-Knappe, Hemmingen, all of (DE)

(73) Assignee: Wolf-Georg Forssmann, Hannover (DE)

( * ) Notice: Subject to any disclaimer, the term of this patent is extended or adjusted under 35 U.S.C. 154(b) by 0 days.

(21) Appl. No.: 09/319,267

(22) PCT Filed: Dec. 10, 1997

(86) PCT No.: PCT/EP97/06881

§ 371 (c)(1),
(2), (4) Date: Jan. 11, 2000

(87) PCT Pub. No.: WO98/25966

PCT Pub. Date: Jun. 18, 1998

(30) Foreign Application Priority Data

Dec. 13, 1996 (EP) .............................. 96120024

(51) Int. Cl.⁷ .............................................. A01N 37/18
(52) U.S. Cl. ............................... 514/2; 514/2; 514/12; 514/13; 514/15; 514/54; 514/62; 514/440; 435/69.5; 435/325; 435/320.1; 435/69.3; 536/23.5; 536/23.4; 536/23.1; 530/350; 530/300; 424/85.1; 600/9
(58) Field of Search .......................... 424/85.1; 530/350, 530/359; 514/2, 13, 12, 54, 62, 440, 15; 435/325, 69.5, 320.1, 69.3; 536/23.5, 23.4, 23.1; 600/9

(56) References Cited

U.S. PATENT DOCUMENTS

| | | | |
|---|---|---|---|
| 5,306,709 A | * 4/1994 | Gewritz | 514/12 |
| 5,677,136 A | * 10/1997 | Simmons et al. | 435/7.24 |
| 5,856,444 A | * 1/1999 | Kawakitz et al. | 530/350 |
| 5,981,231 A | * 11/1999 | Wei et al. | 435/69.5 |

FOREIGN PATENT DOCUMENTS

| | | | |
|---|---|---|---|
| WO | 93/09799 | | 5/1993 |
| WO | 4344387 | * | 12/1993 |
| WO | 94 24285 | | 10/1994 |
| WO | 94 28916 | | 12/1994 |
| WO | 95 17092 | | 6/1995 |
| WO | 96 19234 | | 6/1996 |
| WO | 97 06817 | | 2/1997 |
| WO | WO 96/19234 | * | 10/1997 |
| WO | WO95/17092 | * | 1/1999 |
| WO | WO 94/28916 | * | 11/1999 |

OTHER PUBLICATIONS

Gewritz et al., Blood, vol. 86, No. 7, pp. 2559–2567, Oct. 1, 1995.*

Baggiolini, "Chemokines and leukocyte traffic", Nature, vol. 392, Apr. 9, 1998.

Detheux, et al., "Natural Proteolytic Processing of Hemofiltrate CC Chemokine 1 Generates a Potent CC Chemokine Receptor (CCR)1 and CCR5 Agonist with Anti–HIV Properties", J. Exp. Med., vol. 192, No. 10, Nov. 20, 2000.

S.D. Wolpe et al., "Macrophage inflammatory proteins 1 and 2: members of a novel superfamily of cytokines", The FASEB Journal, vol. 3, Dec. 1989, pp. 2565–2573.

B.I. Lord et al., "Macrophage inflammatory protein: its characteristics, biological properties and role in the regulation of haemopoiesis", International Journal of Hematology, vo. 57, 1993, pp. 197–206.

M.G. Hunter et al., "BB–10010: An Active Variant of Human Macrophage Inflammatory Protein–1alpha wiht Improved Pharmaceutical Properties", Blood, vol. 86, No. 12, Dec. 15, 1995, pp. 4400–4408.

* cited by examiner

Primary Examiner—Karen Cochrane Carlson
Assistant Examiner—Hope A. Robinson
(74) Attorney, Agent, or Firm—Arent Fox Kintner Plotkin Kahn

(57) ABSTRACT

The present invention relates to the use of polypeptides of the MIP (macrophage inflammatory proteins) class for the treatment of diseases involving a pathological change of thrombocytopolesis, especially for the treatment of thrombocytopenia.

15 Claims, No Drawings

USE OF POLYPEPTIDES FOR TREATING THROMBOCYTOPENIA

The present invention relates to the use of polypeptides of the MIP (macrophage inflammatory proteins) class for the treatment of diseases involving a pathological reduction of thrombocytopoiesis.

Thrombocytes (platelets) play a key role in blood clotting and wound healing. Therefore, thrombocytic diseases can lead to hemostatic disorders and thus to massive hemorrhages. It is generally distinguished between thrombocytopenias, in which the platelet count is reduced, and thrombocytic dysfunctions, in which the function of platelets is impaired, in spite of normal counts.

Possible causes of thrombocytopenia include reduced or lacking megakaryocytes in the bone marrow, reduced platelet production, sequestration of platelets in the spleen, increased thrombocytolysis, increased platelet consumption or dilution of the platelet pool. Irrespective of the etiology, severe thrombocytopenia results in skin hemorrhages in the form of multiple petechiae, which are usually most pronounced at the lower legs, and isolated little ecchymoses following trivial traumata. More serious are mucosal hemorrhages (nosebleeding; bleedings in the gastrointestinal tract, in the urogenital tract and in the vagina) and bleedings following surgical interventions. Depending on the extent of thrombocytopenia, severe gastrointestinal bleedings and bleedings into the central nervous system with life-threatening consequences can occur.

Thrombocytopenias can be observed in a variety of diseases and in certain therapeutic treatments. Reduced thrombocytopoiesis can occur as a result of, e.g., myelosuppressive therapy (irradiation, chemotherapy, especially high-dose therapy), bone marrow transplantation, leucemia, anemia (aplastic anemia, Fanconi's anemia etc.), or also following abuse of alcohol. Increased platelet consumption or thrombocytolysis can be the result of diseases such as idiopathic thrombocytopenic purpura, infections (thrombocytopenia upon HIV infection, sepsis etc.), immunological basic diseases (auto-immune diseases, such as systemic lupus erythematosus), chronical leucemia or malignant lymphomas. A reduced platelet count can also occur as a medicament-induced thrombocytopenia upon administration of, for example, heparin, quinidine, sulfonamides, oral antidiabetics, gold salts or rifampicin.

Within the scope of diagnostics in clinical chemistry, the determination of cell counts in the peripheral blood picture provides the essential parameters for establishing the extent of thrombocytopenia, and for obtaining first indications of possible causes. Thus, for example, an increased proportion of large platelets (determinable from a blood smear or by measuring the average platelet volume in an electronic blood cell analyzer) indicates a compensatorily increased platelet production. This is often found in secondary thrombocytopenias due to increased lysis or consumption of platelets. In severe thrombocytopenias from any cause, the bleeding time is prolonged. However, in patients with moderate thrombocytopenia (e.g., 50,000 platelets/$\mu$l), a determination of bleeding time can provide valuable information. In this case, a highly prolonged bleeding time indicates that antibody loading of the platelets evidently results in a functional disorder of the circulating platelets. Another diagnostic criterion is provided by examinations of bone marrow punctures. Thrombocytopenias can then be evaluated by the number and appearance of the megakaryocytes.

For a treatment of thrombocytopenias, the primary causes must be recognized and corrected, e.g., in medicament-induced thrombocytopenias, by a quick discontinuation of the medicament causing the thrombocytopenia, or through the recognition and treatment of an infection with endotoxin-producing Gram-negative germs. If the thrombocytopenia is the consequence of a megakaryopoietic disorder and thus a reduced production of platelets, e.g., following chemotherapy, the platelet count can mostly be increased for a period of 2–3 days by the administration of platelet concentrates. For treating thrombocytopenia, platelet concentrates are administered either continuously (1 to 2 units per hour) or in larger quantities in intervals of several hours, e.g., 6 to 8 units every 4 to 6 hours. For prophylaxis, however, platelet concentrates should be employed reservedly, since their effectivity can drop off upon repeated use because of the development of platelet allo-antibodies. Also, in transfusions, the risk of an infection must not be neglected. If a quick regeneration of the bone marrow function cannot be expected, platelet transfusion should be employed only for the treatment of a clinically manifest tendency to bleed. In thrombocytopenias due to increased platelet consumption, platelet transfusions should be given prophylactically only in exceptional cases, since the platelets are reeliminated from the circulation within one to several hours in such diseases. In the treatment of heparin-induced thrombocytopenia, transfused platelets may also result in the formation of platelet-fibrin thrombi and thus in severe thrombophilia.

Polypeptides of the MIP (macrophage inflammatory proteins) class are known from WO 95/17092. These polypeptides are secreted, for example, by macrophages or lymphocytes if they are stimulated by Gram-negative bacteria, lipopolysaccharides or concanavalin A. WO 95/17092 describes such polypeptides and their use for the preparation of medicaments for the treatment of infections, cancers, inflammations, myelopoietic dysfunctions or auto-immune diseases. In particular, in connection with hematopoiesis, the inhibition of bone marrow stem cells by MIPs is described, for example, for treating myeloproliferative diseases. The inhibitory effect of MIPs on stem cell proliferation is also described as a therapeutic principle in the treatment of cancer, for tranquilizing stem cells by a preliminary MIP administration and thus protecting them from the side-effects of chemotherapy. In addition, WO 95/17092 describes inhibitors and antagonists of such polypeptides which are intended to neutralize MIP-caused bone marrow suppression and thus to be employed for the treatment of, e.g., aplastic anemia or myelodysplastic syndrome. A treatment of thrombocytosis by the administration of MIPs is to be achieved by increasing the vascular permeability in the periphery and thus increased sequestration of platelets. In a recently released meeting abstract, it is reported that the maturation of progenitor cells of monocytes/macrophages is inhibited in the presence of MIP 1$\gamma$, an MIP which is known from WO 95/17092. Consequently, MIP 1$\gamma$ is designated as an M-CIF (macrophage colony inhibition factor).

Further, another MIP fragment with the designation of HCC-1 is known from DE 43 44 387. This fragment is a polypeptide which comprises the sequence of MIP-3 (1–69), N-terminally extended by five additional amino acids. This peptide is therapeutically employed for the treatment of disorders in the migration of cells, diseases of the immune system, tumors, and dysfunction of regulatory growth factors.

From WO 97/06871, it is known that an enhanced regeneration of the hematopoietic system in connection with myelosuppressive therapy can be achieved by the continuous administration of stem cell chemokines (SCC). As stem cell chemokines, there are mentioned, for example, the proteins LD78 (huMIP-1α), muMIP-1α, MIP-1β, IL-8, GRO, NAP-2, MCAF, ENA78, PF4, GCP-2, INPROL, MCP-1, MCP-2 and MCP-3 and their analogues. The regeneration of the hematopoietic system is defined as being satisfactory when the counts of neutrophiles, platelets and/or progenitor cells have increased to a range of more than 25% of their normal values. However, the administration of the stem cell chemokines is described only in connection with myelosuppressive therapy (MT), especially before starting the MT, during the MT and immediately after the MT.

In WO 96/19234, the combined use of CxC chemokines and of hematopoiesis-stimulating agents, such as CSFs, for enhancing the release and mobilization of hematopoietic cells from the bone marrow is described. Such combination preparations are employed in treatments in which an enrichment of blood with hematopoietic stem cells is therapeutically useful, e.g., in peripheral blood stem cell transplantations and for enhancing the immune response.

In WO 94/28916, the use of stem cell inhibitors (SCI), such as muMIP-1α or huMIP-1α and their analogues, for enhancing the release and mobilization of hematopoietic stem cells is described. The stem cell inhibitors are used, for example, in the treatment of neutropenias which occur in connection with chemotherapy.

Surprisingly, it has now been found that the polypeptides of the MIP class and their derivatives cause a significant and specific increase of the platelet count and thus can be used for the preparation of medicaments for the treatment of conditions which generally involve a reduction of platelet counts. This includes primarily those diseases which involve either a megakaryopoietic disorder or a pathological reduction of thrombocytopoiesis. In this connection, these polypeptides are especially used for the treatment of thrombopenias, such as thrombopenias induced by chemotherapy or irradiation; or thrombopenias related with bone marrow transplantations, viral or retroviral infections, autoimmune diseases and anemias. The therapeutical effect of these polypeptides was demonstrated in vivo through stimulation of thrombocytopoiesis. After a preliminary treatment with chemotherapeutical agents, a quicker regeneration of the progenitor cells in the bone marrow and thus a significantly shortened duration of the thrombopenic condition could be achieved.

Useful derivatives of said MIPs include such polypeptides which are derived by extension, deletion or substitution of one or more amino acids (cf., for example, WO 94/28916; WO 95/17092; WO 93/09799; WO 94/24285; The Faseb Journal 1989, 3: 2565–2573; Int. J. Hematol. 1993, 57: 197–206; Blood 1995, 86(12): 4400–4408). Such fragments or derivatives include, for example, those polypeptides in which one or more amino acids are replaced by naturally occurring or other amino acids, one or more of the amino acids have a substituent, or the polypeptide is coupled to other compounds (such as polyethylene glycol), in order to increase its half-life, for example. Further, the polypeptides can be N-terminally and/or C-terminally extended or shortened by one or more amino acids, provided that the biological activity of the polypeptides with respect to the stimulation of thrombocytopoiesis is essentially retained. In particular, such extensions include leader sequences or secretory sequences, wherein up to 40 amino acids, preferably up to 20 or 10 amino acids can precede the sequence of the mature polypeptide at the N terminus. Fragments are those peptides which are derived by N-terminal or C-terminal truncations of the sequence of the mature protein, wherein the truncations may include from 1 to 10 amino acids. Particularly preferred is the peptide HCC-1.

The biological activity of the fragments is described by way of example with the aid of examinations on the polypeptide HCC-1:

EXAMPLE

Stimulation of thrombocytopolesis by HCC-1 following busulfan treatment of Balb/c mice

Materials and Methods

Balb/c mice (female, 6–8 weeks old, 17 g body weight) are intraperitoneally administered busulfan at a dosage of 20 mg/kg in one single dose on day 0. Cremophor EL is used as a solubilizer for busulfan. Beginning with day 1 and up to day 15, the animals are intraperitoneally administered HCC-1 in PBS/1% BSA as the solvent once a day. The administered doses are between 0.01 and 10 µg/mouse. Control animals are given only the solvent PBS/1% BSA once a day i.p. At the stated times, 20 µl of whole blood is removed from the animals via the retrobulbar route, and the various blood parameters are determined in a blood analyzer (Contraves Autolyzer 801).

Result

Following application of the cytostatic agent busulfan, a temporary thrombocytopenia is induced in mice with a suitable dosage (Morley and Blake, Oyekan and Onabanjo). The development of the platelet count in peripheral blood of Balb/c mice is plotted against time after administration of a single dose of 20 mg/kg busulfan. From the graphical representation, it can be seen that, beginning with day 8 after the injection, the platelet counts in the busulfan control decrease and reach their minimum already between days 11 and 13. The reduction of the PLT values is about 60%. Then, the platelet counts again increase until day 21, a rebound phenomenon cannot be observed. Until day 35, the PLT counts in the busulfan group remain below the untreated control and do not reach the initial level again.

After busulfan application and subsequent daily administration of HCC-1, a decrease of the platelet counts is observed also from day 8. However, the values reached for the minimum are above the busulfan control for all dosages of HCC-1. In addition, the time elapsed until the platelet counts again increase is significantly shortened so that PLT counts of about $800 \times 10^6$/ml can again be measured already at day 15 in the group with HCC-1, 1 µg/mouse. In the further course of the experiment, the PLT counts in the HCC-1-treated groups are above the busulfan control and again reach the level of the untreated control animals from about day 30. If $700 \times 10^6$ PLT/ ml is defined as the limit, the duration and extent of the thrombopenia (measured as the area below the curve) is reduced by up to 70% by the administration of HCC-1 as compared to the busulfan control.

TABLE 1

Influence of HCC-1 on the extent of thrombopenia in busulfan-treated Balb/c mice

| Busulfan | Therapy | Dosage [per mouse] | Thrombopenia[a] [%] | % reduction |
|---|---|---|---|---|
| + | PBS-BSA | — | 100 | — |
| + | HCC-1 | 10 µg | 45 | 55 |
| + | HCC-1 | 1 µg | 30 | 70 |
| + | HCC-1 | 0.1 µg | 35 | 65 |
| + | HCC-1 | 0.01 µg | 58 | 42 |

[a] = the beginning of thrombopenia was fixed at $700 \times 10^6$ PLT/ml, and the area below the curve was established for each therapy group (n = 8 animals/group)

What is claimed is:

1. A method for treatment of thrombopenia in a subject in need of the treatment, comprising administering a thrombopenia-inhibitory effective amount of an agent to the subject, wherein the agent is HCC-1, wherein the thrombopenia is a pathological reduction of platelet counts.

2. The method according to claim 1, wherein the thrombopenia involves a reduction of megakaryopoiesis.

3. The method according to claim 1, wherein the thrombopenia involves a reduction of thrombocytopoiesis.

4. The method according to claim 1, wherein the thrombopenia is induced by chemotherapy or irradiation.

5. The method according to claim 1, wherein the thrombopenia is induced by a condition selected from the group consisting of a bone marrow transplantation, a viral infection, a retroviral infection, an auto-immune disease and anemia.

6. A method for treatment of thrombopenia in a subject in need of the treatment, comprising administering a thrombopenia-inhibitory effective amount of an agent to the subject, wherein said agent is macrophage inflammatory protein-3 or macrophage inflammatory protein-4, wherein the thrombopenia is a pathological reduction of platelet counts.

7. The method according to claim 6, wherein the thrombopenia involves a reduction of megakaryopoiesis.

8. The method according to claim 6, wherein the thrombopenia involves a reduction of thrombocytopoiesis.

9. The method according to claim 6, wherein said thrombopenia is induced by chemotherapy or irradiation.

10. The method according to claim 6, wherein said thrombopenia is induced by a condition wherein the condition is selected from the group consisting of a bone marrow transplantation, a viral infection, a retroviral infection, an auto-immune disease and anemia.

11. A method for treatment of thrombopenia in a subject in need of the treatment, comprising administering a thrombopenia-inhibitory effective amount of an agent to the subject, wherein said agent is HCC-1 coupled to polyethylene glycol, wherein the thrombopenia is a pathological reduction of platelet counts.

12. The method according to claim 11, wherein the thrombopenia involves a reduction of megakaryopoiesis.

13. The method according to claim 11, wherein the thrombopenia involves a reduction of thrombocytopoiesis.

14. The method according to claim 11, wherein said thrombopenia is induced by chemotherapy or irradiation.

15. The method according to claim 11, wherein said thrombopenia is induced by a condition selected from the group consisting of a bone marrow transplantation, a viral infection, a retroviral infection, an auto-immune disease and anemia.

* * * * *

UNITED STATES PATENT AND TRADEMARK OFFICE
CERTIFICATE OF CORRECTION

PATENT NO. : 6,403,553 B1
DATED : June 11, 2002
INVENTOR(S) : Hans-Georg Opitz et al.

It is certified that error appears in the above-identified patent and that said Letters Patent is hereby corrected as shown below:

Column 2,
Line 58, delete "DE 43 44 387" and substitute therefore -- DE 43 44 397 --.

Signed and Sealed this

Twenty-second Day of June, 2004

JON W. DUDAS
*Acting Director of the United States Patent and Trademark Office*